US012700331B2

(12) United States Patent
Belykh et al.

(10) Patent No.: US 12,700,331 B2
(45) Date of Patent: Aug. 4, 2026

(54) SYSTEMS AND METHODS FOR A NEUROSURGICAL SIMULATION MODEL FOR SURGICAL TRAINING

(71) Applicant: Dignity Health, San Francisco, CA (US)

(72) Inventors: Evgenii Belykh, San Francisco, CA (US); Mark C. Preul, San Francisco, CA (US); Michael T. Lawton, San Francisco, CA (US); Sarah McBryan, San Francisco, CA (US)

(73) Assignee: Dignity Health, San Francisco, CA (US)

( * ) Notice: Subject to any disclaimer, the term of this patent is extended or adjusted under 35 U.S.C. 154(b) by 1000 days.

(21) Appl. No.: 17/905,383

(22) PCT Filed: Mar. 9, 2021

(86) PCT No.: PCT/US2021/021540
§ 371 (c)(1),
(2) Date: Aug. 31, 2022

(87) PCT Pub. No.: WO2021/183538
PCT Pub. Date: Sep. 16, 2021

(65) Prior Publication Data
US 2023/0112951 A1 Apr. 13, 2023

Related U.S. Application Data

(60) Provisional application No. 62/987,018, filed on Mar. 9, 2020.

(51) Int. Cl.
| | |
|---|---|
| *G09B 23/30* | (2006.01) |
| *A61B 17/00* | (2006.01) |
| *A61B 34/10* | (2016.01) |

(52) U.S. Cl.
CPC .... *G09B 23/30* (2013.01); *A61B 2017/00526* (2013.01); *A61B 2034/105* (2016.02)

(58) Field of Classification Search
CPC ................................ G09B 23/28; G09B 23/30
See application file for complete search history.

(56) References Cited

U.S. PATENT DOCUMENTS

| | | | | |
|---|---|---|---|---|
| 9,697,639 | B2 * | 7/2017 | Masumoto | .............. G06T 19/00 |
| 10,181,270 | B1 * | 1/2019 | Fuller | .................... G09B 23/30 |
| 10,319,259 | B2 * | 6/2019 | Kerins | ................ G09B 23/303 |
| 10,726,742 | B2 * | 7/2020 | Wang | .................... B33Y 80/00 |
| 10,898,272 | B2 * | 1/2021 | Dekel | .................... A61B 1/267 |
| 11,169,504 | B2 * | 11/2021 | Radjou | .............. G05B 19/4099 |
| 11,373,552 | B2 * | 6/2022 | Magsood | .............. G01R 33/58 |

(Continued)

FOREIGN PATENT DOCUMENTS

WO WO-2018222779 A1 * 12/2018 ............. G16H 50/50

OTHER PUBLICATIONS

Patent Cooperation Treaty, International Search Report and Written Opinion, International Application No. PCT/US2021/021540, Date of mailing Aug. 10, 2021, 10 pages.

*Primary Examiner* — Kurt Fernstrom
(74) *Attorney, Agent, or Firm* — Polsinelli PC

(57) ABSTRACT

Various embodiments of an anatomical model suitable for microsurgical training are disclosed. The anatomical model includes predetermined ergonomic features that accommodate training of a surgical task.

4 Claims, 7 Drawing Sheets

(56) References Cited

U.S. PATENT DOCUMENTS

| | | | |
|---|---|---|---|
| 11,521,519 B2 * | 12/2022 | Mathaneswaran | G09B 23/30 |
| 11,741,854 B2 * | 8/2023 | McAlpine | G09B 23/30 |
| | | | 434/272 |
| 11,875,704 B2 * | 1/2024 | Dixon | G09B 23/34 |
| 12,062,296 B2 * | 8/2024 | Pirlot de Corbion | |
| | | | G09B 23/286 |
| 2012/0224755 A1 | 9/2012 | Wu | |
| 2015/0025666 A1 | 1/2015 | Olivieri et al. | |
| 2015/0093734 A1 * | 4/2015 | Kaouk | A61B 34/10 |
| | | | 434/267 |
| 2015/0352250 A1 * | 12/2015 | Dalman | A61L 27/50 |
| | | | 523/115 |
| 2016/0155364 A1 * | 6/2016 | Piron | G01R 33/58 |
| | | | 434/270 |
| 2016/0287339 A1 * | 10/2016 | Bin Abdul Rahman | |
| | | | A61B 8/00 |
| 2017/0360578 A1 * | 12/2017 | Shin | G09B 23/286 |
| 2019/0355280 A1 * | 11/2019 | Champ | B29C 64/393 |
| 2020/0316850 A1 * | 10/2020 | Seitz | G09B 23/30 |

* cited by examiner

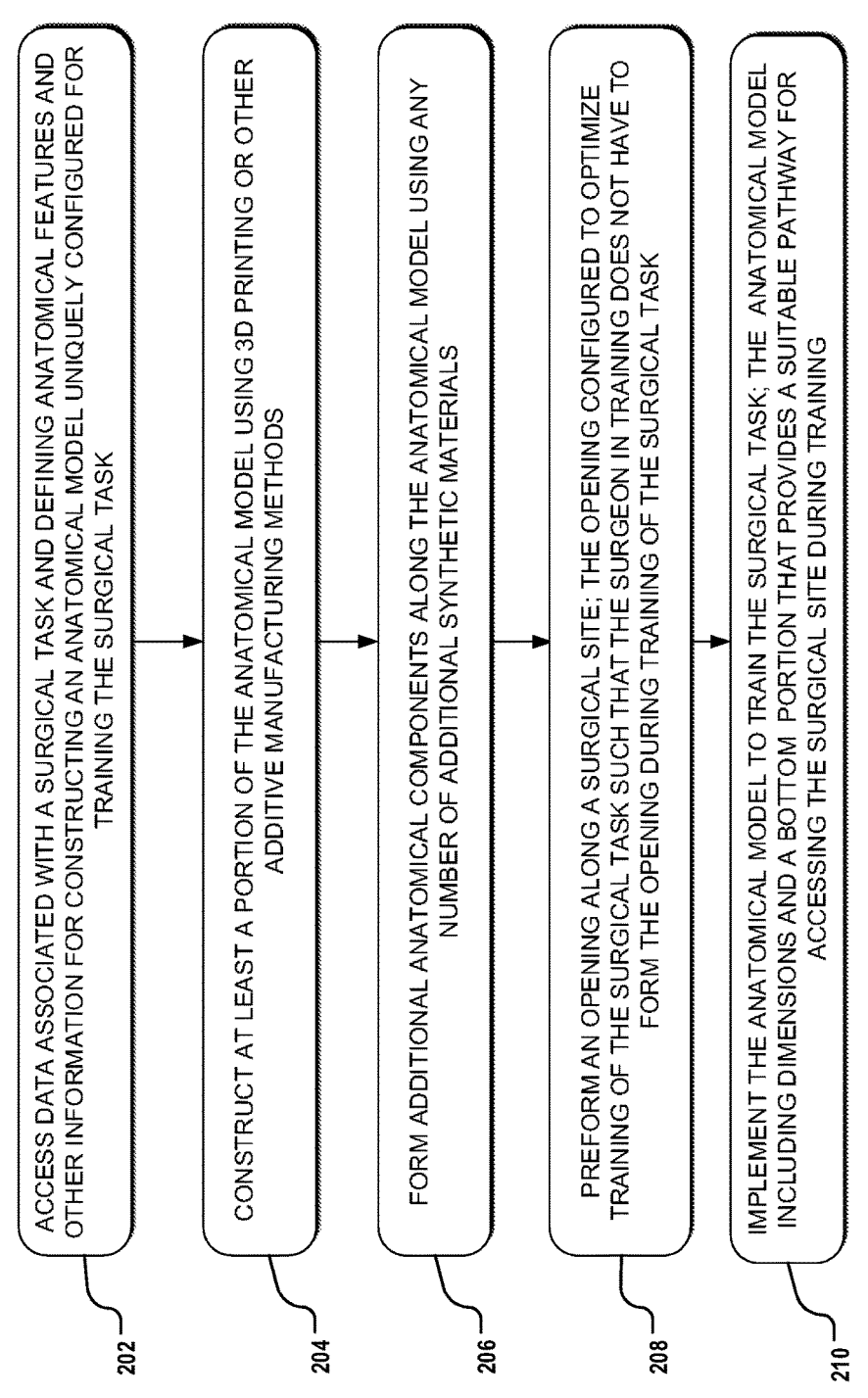

200

ACCESS DATA ASSOCIATED WITH A SURGICAL TASK AND DEFINING ANATOMICAL FEATURES AND OTHER INFORMATION FOR CONSTRUCTING AN ANATOMICAL MODEL UNIQUELY CONFIGURED FOR TRAINING THE SURGICAL TASK

202

CONSTRUCT AT LEAST A PORTION OF THE ANATOMICAL MODEL USING 3D PRINTING OR OTHER ADDITIVE MANUFACTURING METHODS

204

FORM ADDITIONAL ANATOMICAL COMPONENTS ALONG THE ANATOMICAL MODEL USING ANY NUMBER OF ADDITIONAL SYNTHETIC MATERIALS

206

PREFORM AN OPENING ALONG A SURGICAL SITE; THE OPENING CONFIGURED TO OPTIMIZE TRAINING OF THE SURGICAL TASK SUCH THAT THE SURGEON IN TRAINING DOES NOT HAVE TO FORM THE OPENING DURING TRAINING OF THE SURGICAL TASK

208

IMPLEMENT THE ANATOMICAL MODEL TO TRAIN THE SURGICAL TASK; THE ANATOMICAL MODEL INCLUDING DIMENSIONS AND A BOTTOM PORTION THAT PROVIDES A SUITABLE PATHWAY FOR ACCESSING THE SURGICAL SITE DURING TRAINING

SYSTEMS AND METHODS FOR A NEUROSURGICAL SIMULATION MODEL FOR SURGICAL TRAINING

CROSS REFERENCE TO RELATED APPLICATIONS

This application claims benefit to U.S. provisional patent application Ser. No. 62/987,018, filed on Mar. 9, 2020, which is incorporated by reference in entirety.

FIELD

The present disclosure generally relates to systems and methods associated with anatomical models; and in particular, to a preconfigured, ergonomically-enhanced, neurosurgical anatomical model and methods of forming the same for providing improvements in training of microsurgical skills.

BACKGROUND

Conventional anatomical models do not typically model patient-specific anatomy, and are created in an environment that differs from the real intraoperative field in terms of restrictions and dimensions. Conventional microsurgical training in many cases relies upon training on rats or artificial vessels models that have been used for extended periods of time. However, such methods do not account for unique restrictions of the operating field (e.g., depth, anatomical structures, patient head positioning, etc.). Cadaver training is often viewed as the best surrogate to simulate bypass surgery within the surgical approach; however, work with cadaver material is subject to limitations (such as the need for special laboratory set up and time required to create the approach) which limits its use. In addition, known neurosurgical models often require fixation equipment or require excess preparation time for training.

It is with these observations in mind, among others, that various aspects of the present disclosure were conceived and developed.

SUMMARY

In one embodiment, the present disclosure takes the form of a method of making an anatomical model. The method includes the steps of accessing, by a computing device, first image data defining first anatomical features associated with a first surgical training task; generating, by the computing device, first print data defining a first profile for forming at least a portion of a first anatomical model that includes the first anatomical features and is configured for the first surgical training task; and constructing, by a manufacturing device based on the first print data, at least a portion of the first anatomical model with a first surgical site configured for the first surgical training task. In some embodiments, the first anatomical model includes at least one ergonomic feature configuration that accommodates a first surgical approach that is ergonomically suitable for the first surgical training task.

In some embodiments, the method further includes the steps of accessing, by the computing device, second image data defining second anatomical features associated with a second surgical training task; generating, by the computing device, second print data defining a second profile for forming a second anatomical model that includes the second anatomical features and is configured for the second surgical training task; and constructing, by the manufacturing device based on the second print data, at least a portion of the second anatomical model with a second surgical site configured for the second surgical training task, wherein the second anatomical model including the second anatomical features accommodates a second surgical approach that is ergonomically suitable for the second surgical training task.

The present disclosure may also take the form of a training device for microsurgical training, comprising an anatomical model configured for a surgical task including a plurality of synthetic anatomical components. At least a portion of the plurality of synthetic anatomical components is formed using three-dimensional printing. The plurality of synthetic anatomical components includes a plurality of synthetic brain tissue components; a synthetic skull formed over the synthetic brain tissue components; and a plurality of skin and muscle layers formed over the synthetic skull. In some embodiments, the anatomical model includes a surgical site and at least one ergonomic feature configuration that accommodates a unique surgical approach that is ergonomically suitable for the surgical task.

In some embodiments, the training device further includes an opening preformed along the surgical site of the anatomical model, the opening providing access to the surgical site to accommodate training of the surgical task without a surgeon having to form the opening during training.

The present disclosure may further take the form of a system including a manufacturing device and a computing device that collectively form at least one neurosurgical anatomical model. The manufacturing device may take the form of a three-dimensional (3D) printer, or other such additive manufacturing machine or fused deposition modeling device. The manufacturing device may receive or otherwise access instructions (e.g., print instructions) for manufacturing the anatomical model from the computing device. In some embodiments, the computing device provides the manufacturing device with print data which may define printing instructions for constructing the model with a particular set of anatomical features such that the model is constructed for a unique surgical approach associated with a corresponding surgical training task.

BRIEF DESCRIPTION OF THE DRAWINGS

FIG. 2 is an exemplary process flow for forming and implementing a neurosurgical anatomical model for training.

Corresponding reference characters indicate corresponding elements among the view of the drawings. The headings used in the figures do not limit the scope of the claims.

DETAILED DESCRIPTION

Figure 1A:
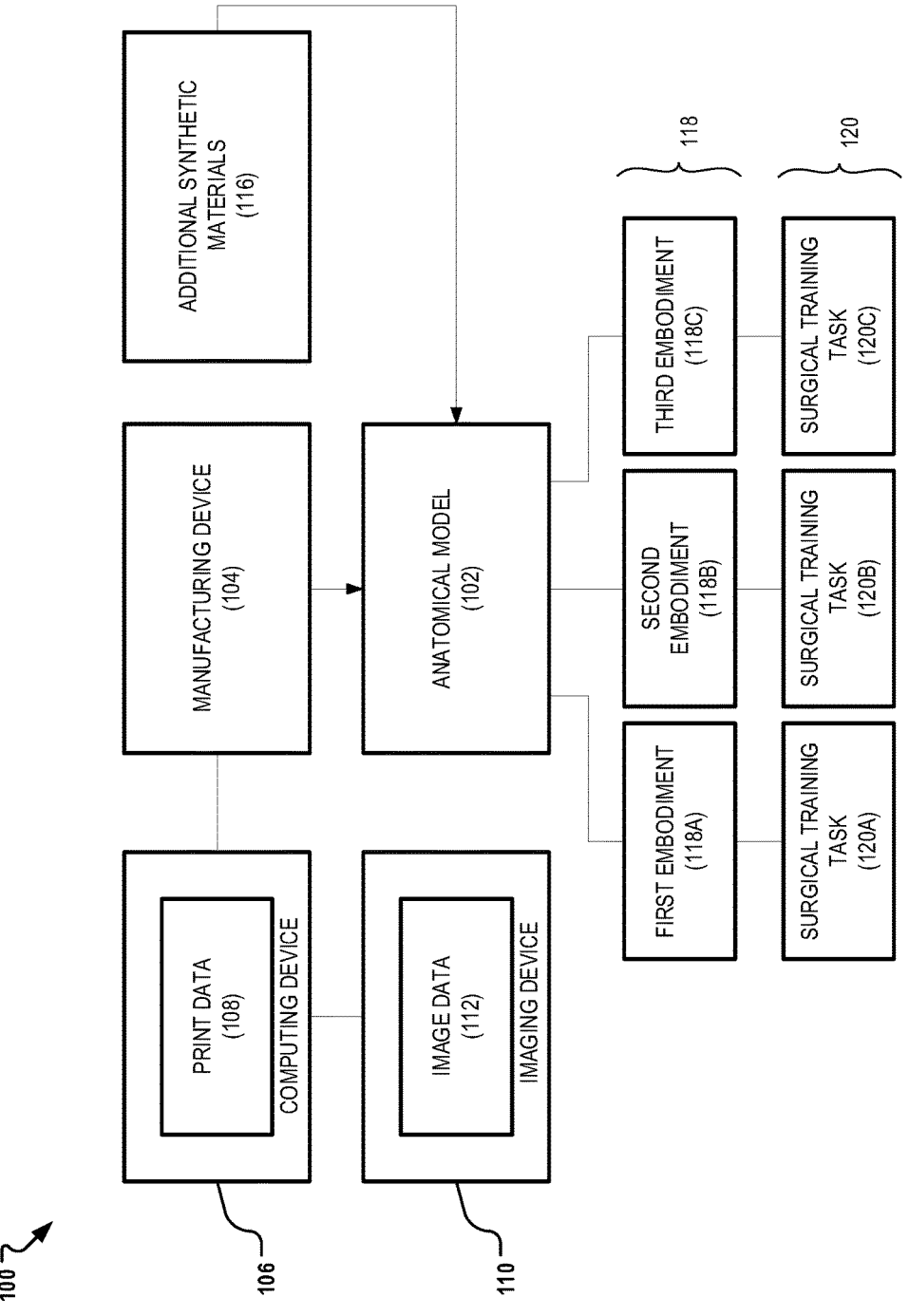
FIG. 1A is a simplified block diagram of a system for forming anatomical models suitable for training of microsurgical methods.

Aspects of the present disclosure relate to embodiments of a neurosurgical anatomical model of the head and brain (and methods thereof) with pre-made approach features. More specifically, the neurosurgical anatomical model is pre-configured for particular approach methodologies and is ergonomically enhanced to simulate the restrictions of the surgical approach and hand position for e.g., bypass surgery. As disclosed herein, the neurosurgical anatomical model is generally configured to accommodate efficient access and repetitive training of the relevant part-task procedural skills involved in various microsurgical methods in a conditioned environment. The neurosurgical anatomical model may further be devoid of certain structures that might otherwise provide a distraction to other concomitant tasks such as approach, creation, dissection, and the like.

In some embodiments, a unique method is employed for constructing the disclosed neurosurgical anatomical model according to the surgical anatomy and approach of real specific patients. For example, a virtual framework/template for constructing the neurosurgical anatomical model may be generated using a particular patient's CT and MRI scans and intraoperative photo and video recording. Subsequently, the neurosurgical anatomical model may be produced by rapid manufacturing technology (3-D printing), injection molding, or other such methods. In some embodiments, each neurosurgical anatomical model is accompanied by narrated pre and post-operative scans, and surgical video of a particular case, to demonstrate in which clinical situation such position and skills are considered necessary and how such case was managed in the real life. Further, each neurosurgical anatomical model may include the synthetic anatomical structure to simulate a human head with predetermined features suitable for a given surgical approach, artificial vessels that could be positioned at the anatomically relevant locations for bypass training, and a video file to illustrate known training methods for use with the model.

In one non-limiting application, the disclosed neurosurgical anatomical model may be used for microanastomosis training in the positions and restrictions of the surgical operating field and may consequently provide an improved means for advanced training of microsurgical skills. In another non-limiting application, the neurosurgical anatomical model may be used for the seven simulation models described in published literature for preferred bypass methods.

With the present novel neurosurgical anatomical model, there is little or no limitation to a particular environment. In other words, the neurosurgical anatomical model is generally portable, and does not require supporting structures or devices. The model does not require materials such a human cadaver or human cadaver model in which a craniotomy or other surgery is necessary. In some embodiments, the neurosurgical anatomical model is patient specific and excludes non-bypass tasks. In some embodiments, the model is not only useful for craniotomy-related tasks, but also for simulation as to the restrictions of the soft tissues, can be positioned on a table, and does not necessitate head-holder fixation.

Referring to FIG. 1A, a general non-limiting system for constructing a neurosurgical anatomical model and implementing the model for training, designated system 100, includes at least one neurosurgical anatomical model, designated model 102. In general, the model 102 may be constructed using one or more of a manufacturing device 104, such as a three-dimensional (3D) printer, or other such additive manufacturing machine or fused deposition modeling process. The manufacturing device 104 may receive or otherwise access instructions (e.g., print instructions) for manufacturing the anatomical model 102 from a computing device 106. In some embodiments, the computing device 106 provides the manufacturing device with print data 108 which may define printing instructions for constructing the model 102 with a particular set of anatomical features such that the model 102 is constructed for a unique surgical approach associated with a corresponding surgical training task, as further described herein.

In some embodiments, an imaging device 110 may be implemented to provide image data 112 to the computing device 106 and/or the manufacturing device 104. The imaging device 110 may include, without limitation, a computerized tomography (CT) scanner, a magnetic resonance imaging machine, an ultrasound machine, 3D surface laser scanning, and the like or combinations thereof. As one specific example, the image data 112 may include CT scans of a cadaver or of a particular living individual. The computing device 106 may be configured to interpret the image data 112 and generate the print data 108 with features for constructing the model 102 to resemble the cadaver/individual of the underlying image data 112 or otherwise construct the model 102 with any number or type of desired anatomical features.

In addition, as shown, any number of additional synthetic materials 116 resembling external or internal anatomies may be added to the anatomical model 102 during or after manufacturing. For example, in some embodiments, the manufacturing device 104 may be implemented to form at least a portion of a synthetic skull. The additional synthetic materials 116, such as urethane rubber, and/or foam layers, may be added or formed around the synthetic skull such that the model 102 includes any number of structural features predetermined to be suitable for simulating training of a particular surgical procedure. The additional synthetic materials 116 may be reusable or replaceable and may include any number of openings or modifications to enhance the model 102 for training applications, as further described herein.

As shown, the model 102 may take the form of any number of embodiments 118, and each of the individual embodiments 118 may be configured to accommodate training of a specific task of a set of surgical training tasks 120. For example as shown, a first embodiment 118A of the model 102 may be formed with dimensions and other structural features suitable for training of a surgical training task 120A, a second embodiment 118B of the model 102 may be formed with dimensions and other structural features suitable for training of a surgical training task 120B, and a third embodiment 118C of the model 102 may be formed with dimensions and other structural features suitable for training of a surgical training task 120C. In some embodiments, at least seven different ones of the embodiments 118 may be constructed to train for the seven (7) primary craniotomy approaches and associated surgical training tasks 120.

Figure 1B:
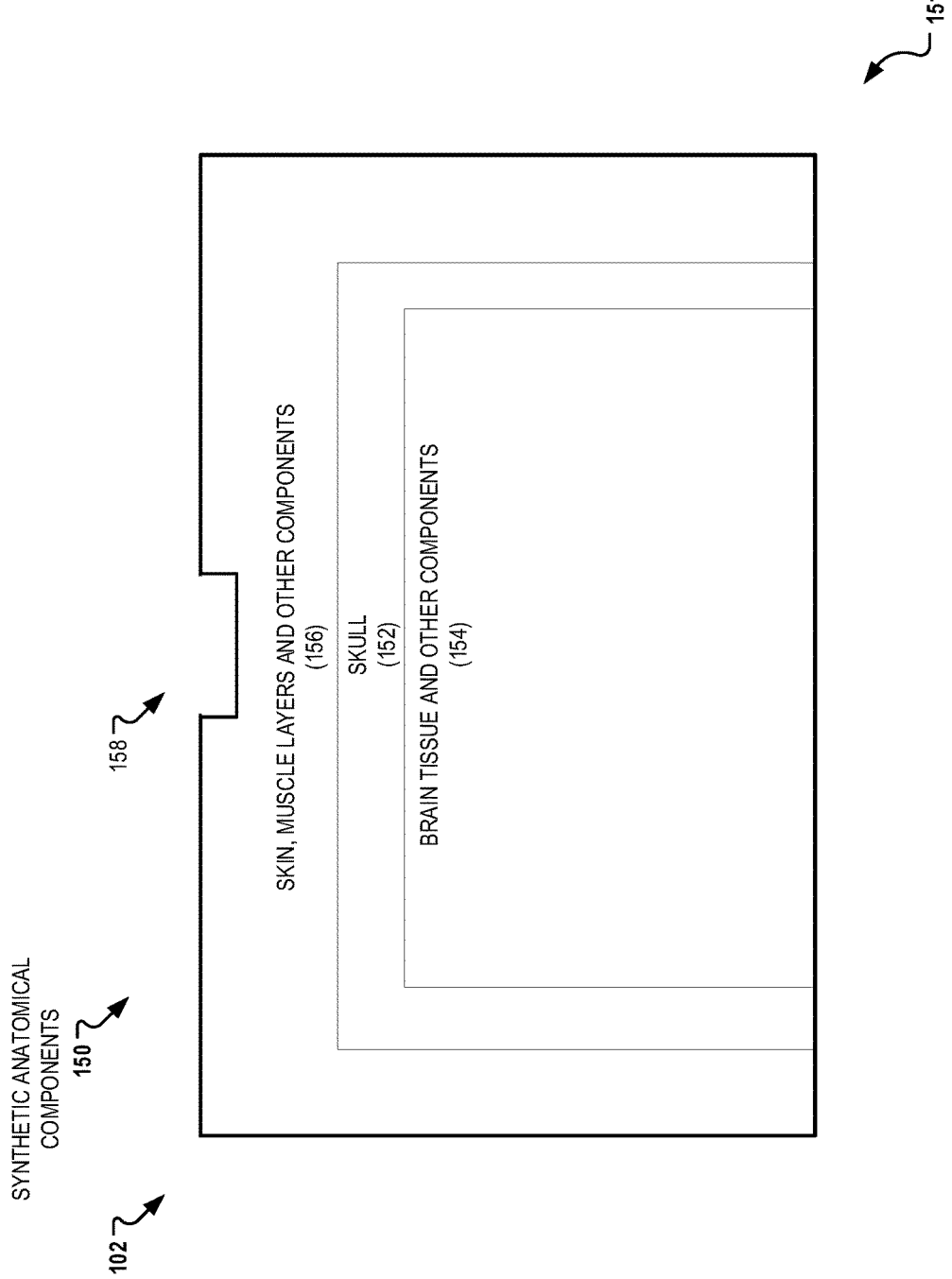
FIG. 1B is a simplified block diagram of a neurosurgical anatomical model ergonomically configured for a realistic and ergonomic surgical approach.

Referring to FIG. 1B, in general, the model 102 includes a plurality of synthetic anatomical components 150, arranged and formed according to a specific, predetermined, ergonomically-enhanced model profile 151 associated with an embodiment 118. In other words, the profile 151 is a blueprint or template that defines the dimensions and physical structures for a unique embodiment 118 so that the embodiment 118 can accommodate a given surgical training task and surgical approach. For example, the profile 151 may define a unique surgical depth, height, and shape of the model 102, and the like. As such, the profile 151 may be based on a particular surgical method, physiological condition, individual patient, or any combinations thereof, and defines the various dimensions and overall shape configuration of the model 102 including a unique depth and/or height of the model 102. For example, in one embodiment 118, the profile 151 of the model 102 defines a partial cranium of a human head, and the profile 151 is designed for practicing a particular surgical task such as micro-suturing of vessels, or any bypass method or procedure that requires practice of a surgeon or clinical professional.

As shown, anatomical components 150 may include a skull 152, i.e., at least a portion of a synthetic skull may be 3D printed or otherwise constructed to form a portion of the model 102. The anatomical components 150 of the model 102 may further include brain tissue 154, and skin and/or muscle layers 156 formed around the skull 152. In some embodiments, the anatomical components 150 of the model 102 may be formed using silicone and urethane molds for specific brain anatomy components. In some embodiments, the anatomical components 150 of the model 102 include synthetic vessels and nerve roots that may be disposable, reusable, or replaceable. The model 102 may further include urethane rubber to simulate portions of the anatomical components 150, and skin and/or muscle layers 156 may be formed using rubber and foam layers. In addition, at least one opening 158, defining a predetermined depth, may be pre-formed along the model 102 to indicate a surgical site for training. Alternatively or in combination, certain anatomical components 150 may be removed, displaced from their natural anatomical position or exposed to create a surgical training environment that allows a surgeon or other individual to train for a particular surgical task efficiently and without the need for fixation equipment or other cumbersome restrictions found with conventional training systems. The model 102 can create a realistic surgical environment for teaching suturing techniques and practice with instrumentation. As described herein, the model 102 may be at least partially manufactured or otherwise constructed using the manufacturing device 104 and may be 3D printed, constructed using injection molding, or may be formed by similar methods or combinations thereof.

Figure 3A:
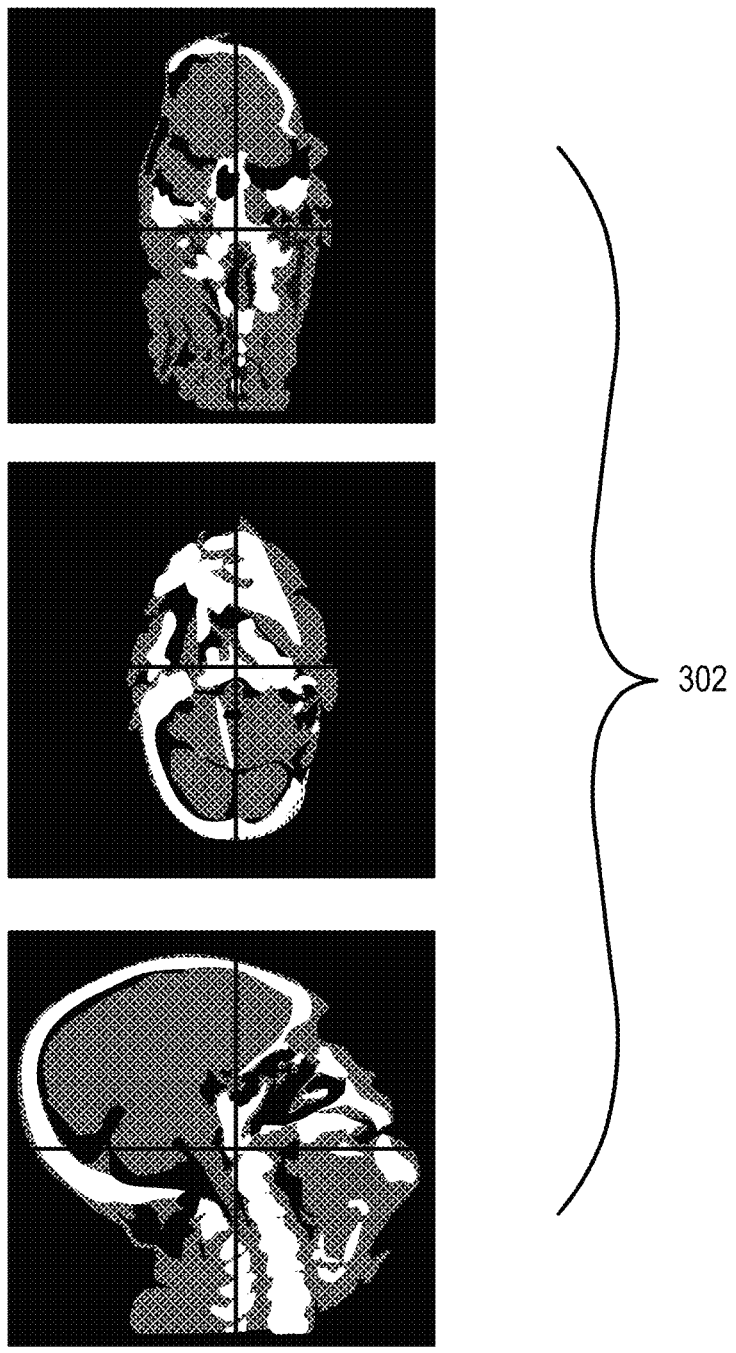
FIGS. 3A and 3B are illustrations showing formation of a neurosurgical anatomical model.
Figure 3B:
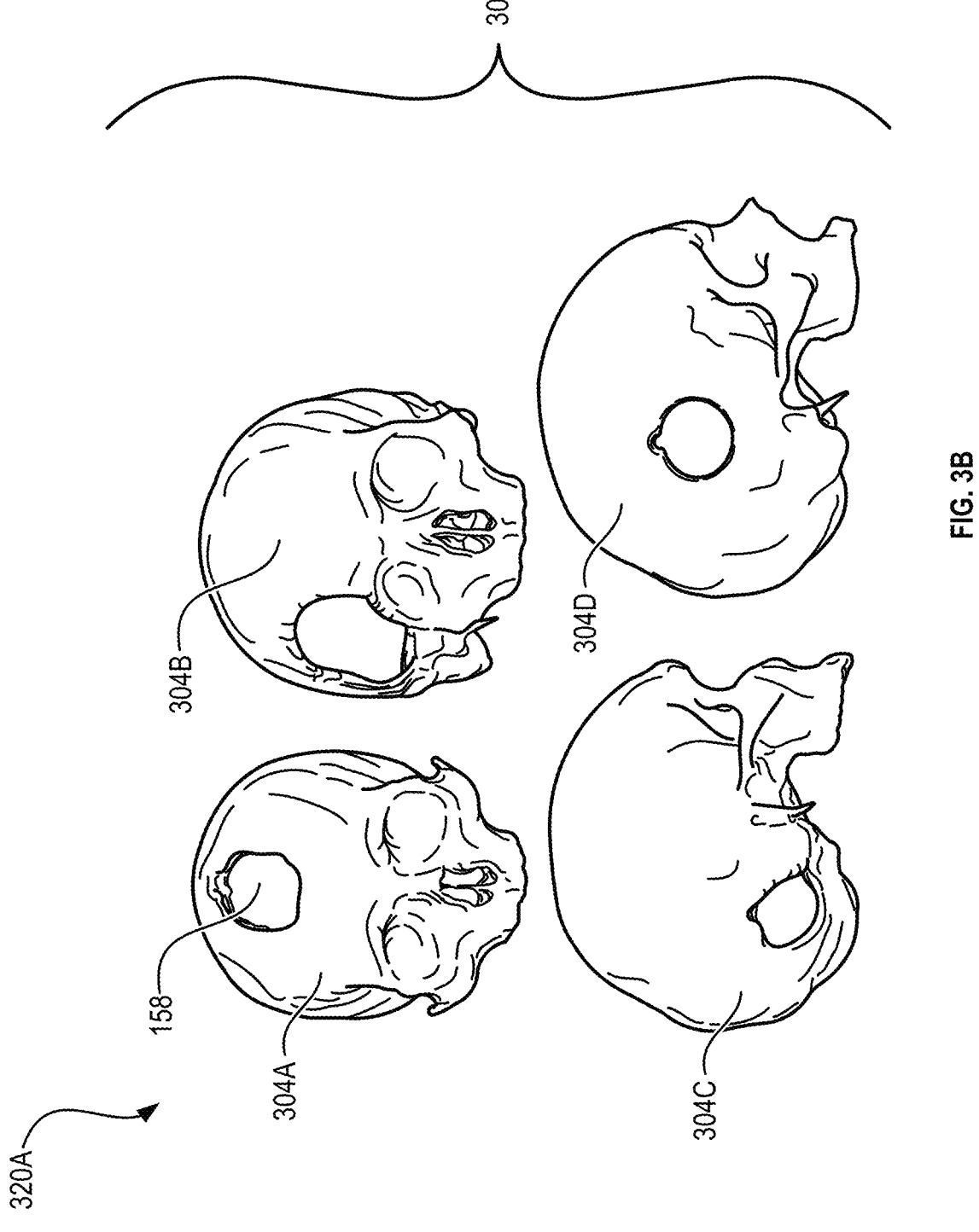

Referring to FIG. 2, with reference to FIGS. 1A-1B and FIGS. 3A and 3B, a non-limiting process for forming and implementing a neurosurgical anatomical model is illustrated. Referring to block 202 of process flow 200 of FIG. 2, the computing device 106 may access data associated with a particular surgical task, defining anatomical features or other information for constructing the model 102 such that the model 102 as constructed is suitable for training the particular surgical task. More specifically, in some embodiments, the computing device 106 is provided with images 302 (FIG. 3A) and/or images 304 (FIG. 3B) or associated information based on CT scans or other image data 112, and the computing device 106 leverages the image data 112 to formulate the profile 151 for the model 102. In this step, the image data 112 may include or be fed with information about exposures and craniotomies performed on cadavers relevant to the surgical task, such that the image data 112 is informative as to predetermined dimensions such as depths measured between key anatomical features related to the particular surgical task for which the model 102 is configured. As indicated in FIG. 3B, the image data 112 may include information from multiple images 304 (shown by example as images 304A-304D) from past implementations of the surgical task on cadavers. In each of those past implementations, execution of the surgical task required formation of the opening 158 in a particular manner and in a particular position along a patient to access a surgical site associated with the surgical task. For example, the image 304A indicates that for execution of a surgical task 320A, the opening 158 was formed along the human skull generally along the forehead in the manner shown. In addition, the image data 112 may indicate that for the past implementations of a surgical task, the opening 158 formed to execute the surgical task averaged or otherwise required a depth of x. As such, the image data 112 informs that the opening 158 formed along the model 102 should also be pre-formed with a depth of x to accommodate training of the surgical task at hand.

Referring to block 204, in some embodiments, the images 302 and/or images 304 acquired may be processed by the computing device 106 or otherwise leveraged to build a blueprint for forming the model 102 consistent with the samples of the image data 112 in the form of print data 108 or otherwise. In other words, the print data 108 defines machine-executable instructions that the computing device 106 can leverage for commanding the manufacturing device 104 to construct the model 102 such that the model 102 resembles the sample cadavers associated with the image data 112. As such, the print data 108 includes any code or machine-executable instructions executable by a processor of the computing device 106 and/or the manufacturing device 104 that may represent one or more of a procedure, a function, a subprogram, a program, a routine, a subroutine, a module, an object, a software package, a class, or any combination of instructions, data structures, or program statements, and the like.

Stated another way, leveraging the print data 108 or some initial digital template for the model 102, the computing device 106 issues at least one command to the manufacturing device 104 to construct at least a portion of the model 102, such as a skull or a portion thereof. In some embodiments, the print data 108 defines or is otherwise produced from a three-dimensional (3D) blueprint for forming the model 102, derived from the image data 112, historical blueprints, or other data sources or combinations thereof. A surgeon or other user may access a 3D digital image associated with the print data via a display, and via the computing device 106, may apply any number of modifications or edits to the 3D digital image and further to the image data 112 and/or print data 108 to adjust any parameters, characteristics, or dimensions of the model 102 ultimately formed. In some cases, the 3D digital image is modified/edited to accommodate unique surgical positions, to apply adjustments to the surgical approach, or to apply optimal physical characteristics to improve the stability and orientation of the actual physical model when the model is placed along a table or other planar object.

Referring to block 206, once at least a portion of the model 102 has been formed, additional synthetic materials 116 may be added to the model 102 such as skin or muscle layers 156, and brain tissue 154. For example, synthetic blood vessels or other anatomical structures may be added to the model 102 that is not formed by the manufacturing device 104. Any number or type of additional structures may be added to the model 102 after the manufacturing device 104 has formed at least a portion of the model 102 to supplement the model 102 with features as desired.

In addition, as indicated in block 208, the model 102 may be modified to accommodate a particular surgical training task 120. For example, the opening 158 or any other such structural modification may be made to the model 102 to increase the training potential of the model 102, and the model 102 may be sculpted and checked for anatomic fidelity. As previously described, the opening 158 may be formed along a predetermined position of the model 102 to expose an interior portion of the model 102 (surgical site)

where the surgical task is ordinarily performed. In this manner, the model 102 includes a configuration that improves and optimizes training because a surgeon training the surgical task 120 can jump right in and train the surgical task 120 without having to form the opening 158.

Referring to block 210, the model 102 as constructed is optimized for training of the given surgical training task 120. For example, a craniotomy facilitating microsurgical suturing or vessels anastomoses may be performed on the model 102 based on key predetermined anatomical landmarks specific to the model 102 and to the given surgical training task 120. As described herein, the model 102 may be configured and structurally designed for a particular surgical training task, such as the surgical training task 120A. For example, at least some portion of the model 102 may include a flat/planar bottom side (FIG. 4A) so that a clinician/ surgeon may train using the model 102 without fixation equipment. In addition, the model 102 may be formed to resemble a human skull with at least some portions of the model 102 pre-removed or exposed so that the practicing/ training surgeon can practice a surgical approach, including surgical manipulation or access to or on a deep brain structure without excess preparatory steps. In other words, the model 102 inherently provides access to or otherwise accommodates the approach for the training of a specific surgical skill inside this model 102. Further for example, the model 102 may be formed with any number of openings or with layers peeled away to facilitate more efficient training.

Figures 4A, 4B:
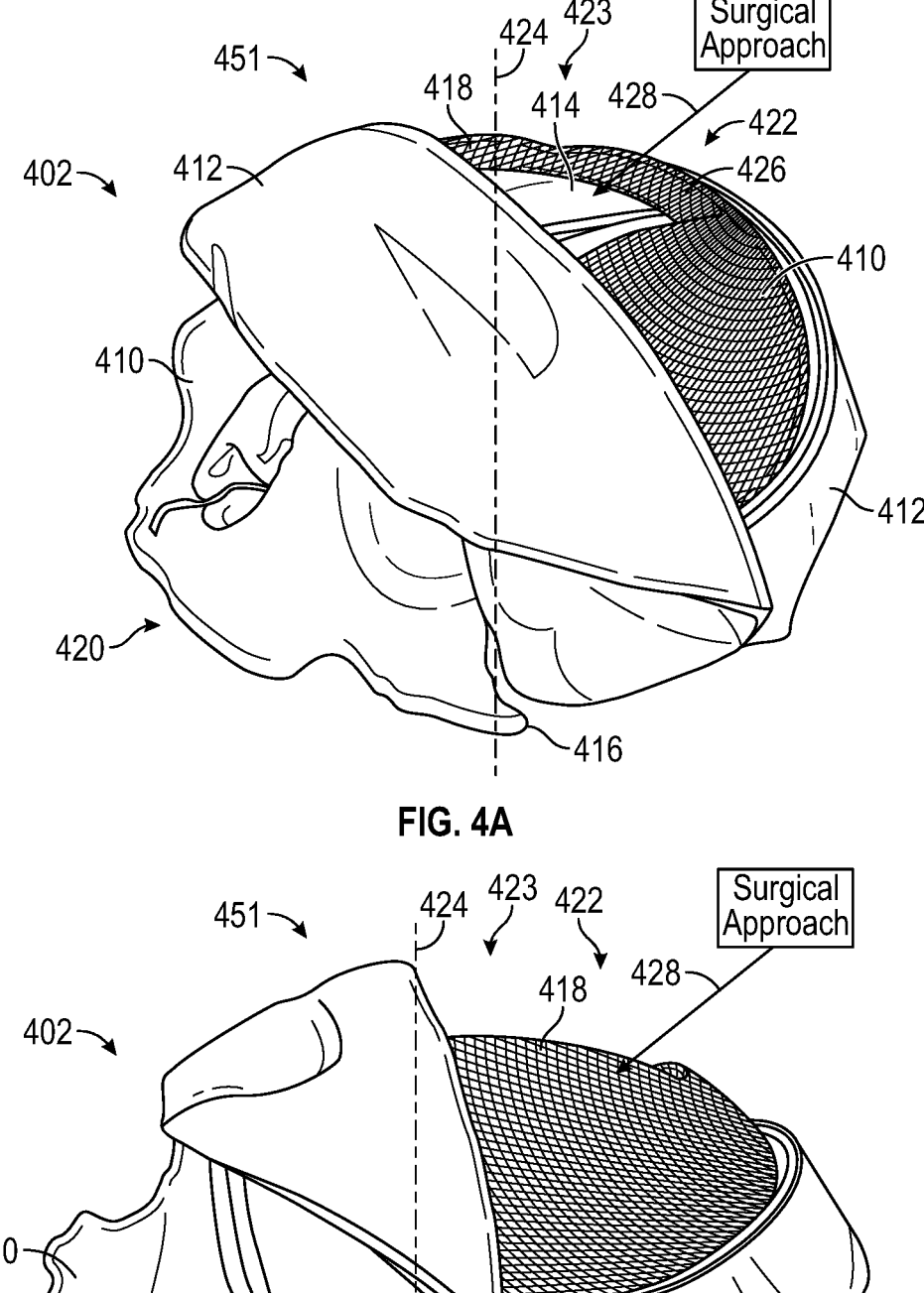
FIGS. 4A-4D are photographs of one embodiment of a neurosurgical model resembling at least a portion of a human head and brain tissue that may be used for a specific surgical training task.
Figures 4C, 4D:
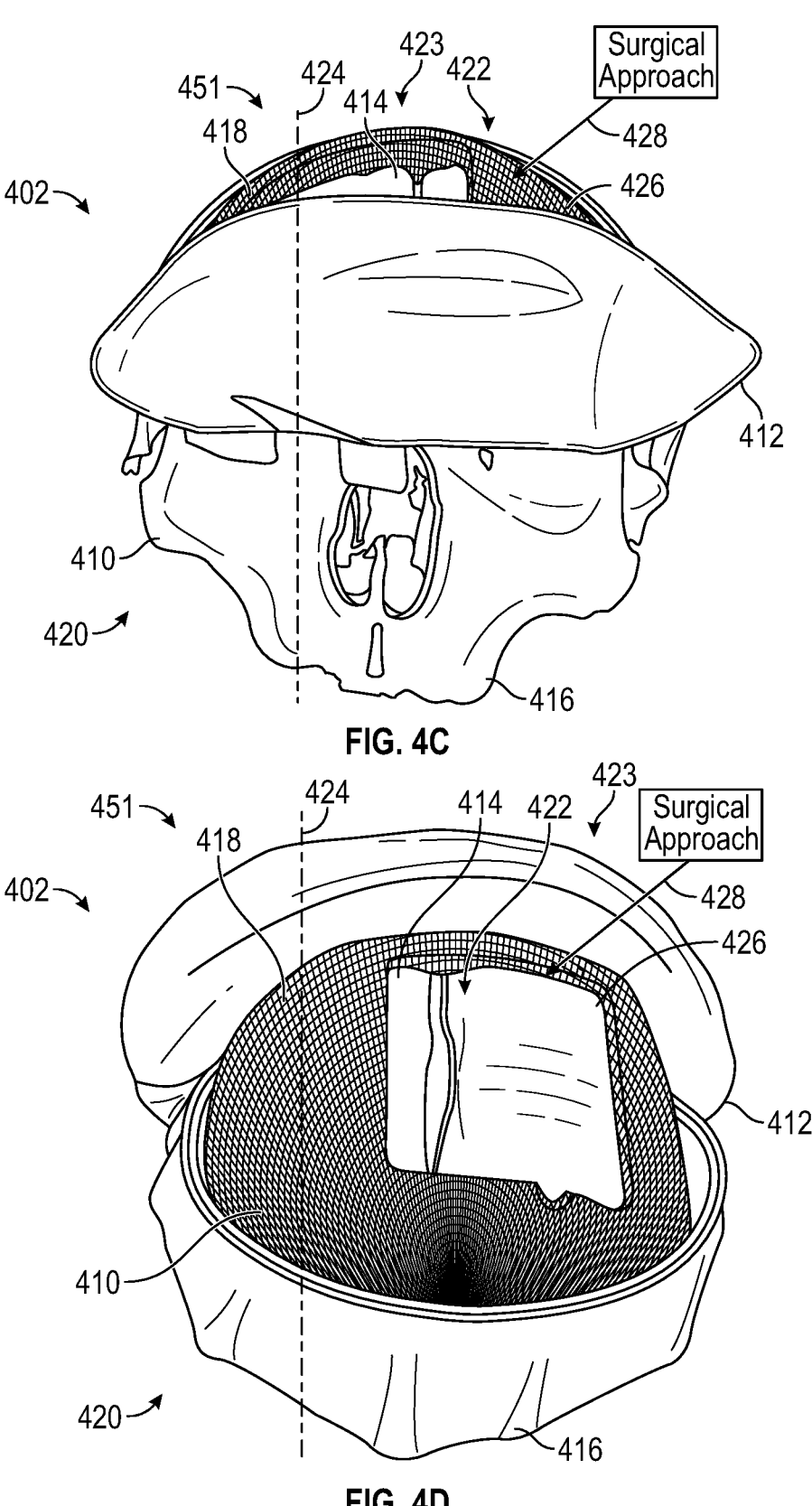

Referring to FIG. 4A, one embodiment 118 of the model 102, designated in FIG. 4A as model 402, is shown, having a plurality of anatomical components 450. In this embodiment, the model 402 relates to the first embodiment 118A and is constructed in view of a profile 451 designed for the surgical training task 120A shown in FIG. 1A, such as a micro-suturing technique. As shown, the model 402 includes a base 410 resembling bone components and/or aspects of a human skull and comprising a rigid material such as plastic. The model 402 further includes synthetic skin tissue 412 implemented in the form of foam and/or urethane rubber. The model 402 further includes synthetic brain tissue 414 positioned underneath the synthetic skin tissue 412 and underneath the based 410.

Uniquely, as demonstrated in FIG. 4A and FIG. 4B, the base 410 of the model 402 defines a bottom side 416 and a top side 418 opposite the bottom side 416, and (as in at least some embodiments) at least a portion of the bottom side 416 is generally planar in its configuration such that the model 402 can be rested securely along a flat surface 420, such as a desk (not shown). In addition, the top side 418 includes a surgical site 422 and an opening 423 (such as the opening 158) where a portion of the synthetic skin tissue 412 is pre-removed from and/or folded away from the synthetic brain tissue 414 as shown. Further, the model 402 generally defines a partial skull configuration, such that the bottom side 416 terminates above the bottom side of a natural human skull (not shown); i.e., the model 402 is devoid of at least a portion of a human skull so that the model 402 can rest along the surface 420 in such a manner so as to simulate an head positioning associated with a particular surgical approach (428) and restrictions of a surgical task the model 402 is designed to train (e.g. surgical training task 120A of FIG. 1A).

In some embodiments, the bottom side 416 of the model 402 is specially constructed to rest flat along the surface 420, and the height/depth 424 of the model 402 between the bottom side 416 and the top side 418 is specifically sized so that a surgeon leaning over the surface 420 or on the handholders (not shown) can approach the surgical site 422 in a manner similar to what would be experienced in a natural surgical setting to engage the surgical training task 120A. In addition, the surgical site 422 and the opening 423 may extend along a predetermined region 426 of the model 402 that is suitable for providing a surgical approach 428 for practicing the surgical training task 120A. Many further related features are contemplated. For example, the model 402 generally and/or the surgical site 422 may be constructed to orient the surgical site 422 towards the practicing surgeon and along the surgical approach 428 in a manner that enhances the training process. The surgical site 422 may further be oriented along any predetermine angle and/or include any other predetermined structural characteristics that improves practice of the surgical training task 120A. As described herein, the opening 423 may be pre-formed and may include any shape, depth, or configuration suitable for providing efficient access to the surgical site 422 to optimize training.

The models described herein (e.g., model 102, and model 402) include various novel features that provide technical improvements over conventional anatomical models and training methods. In particular, the model 102 and the model 402 each provides ease of training and an education platform that can be easily and swiftly deployed, and does not require fixing devices or mechanisms for holding the model 102 and the model 402 in place during use. Put simply, the model 102 is portable, and can be placed along a flat surface of choice to commence training of any surgical method or task for which the models are configured and constructed. Further, the model 102 and the model 402 each provide realistic ergonomics in a surgical setting. For example, the model 402 is constructed with dimensions and a shape configuration (defined by the profile 451) that allows a practicing surgeon to approach simulated anatomical components, such as the synthetic brain tissue 414 proximate the surgical site 422, in an ergonomic manner that resembles the ergonomics of a natural/real clinical setting for a surgical training task 120A associated with the model 402. In other words, the model 402 (and the model 102) is preconfigured to facilitate the ergonomics of the surgical approach 428 associated with the surgical training task 120A. All of these features facilitate a more realistic training setting for the model 102 and the model 402 compared with conventional training for table-top micro suturing. In some embodiments, the models 102 and 402 accommodate the practice of micro-suturing techniques using 8-0, 9-0 and 10-0 Prolene sutures.

In one embodiment, the system 100 includes a set of simulation models identical to or similar to the model 102 in order to model the head and brain with pre-made approach, and to simulate the restrictions of the surgical approach and hand position for bypass surgery. These models may be used for or part of training (in any capacity) for bypass skills in anatomy and an approach-conditioned environment. Additionally, these models of the system 100 provide fast access to allow repetitive training of the relevant part-task procedural skills directly (e.g., microanastomosis).

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. A method of making anatomical models for surgical training, comprising:

accessing, by a computing device, first image data defining first anatomical features associated with a first surgical training task;

generating, by the computing device, first print data from a three-dimensional digital representation of a first anatomical model based at least in part on the first image data, the three-dimensional digital representation defining a first profile for the first anatomical model, the first profile defining;

(i) a base of the first anatomical model including a bottom side, the bottom side being generally planar, (ii) a first surgical site of the first anatomical model extending along a predetermined region of the first anatomical model, and (iii) a distance between the bottom side and the first surgical site selected based at least in part on exposure data associated with implementations of the first surgical training task such that, when the bottom side rests on a planar support surface, the first surgical site is presented at a predetermined height and approach angle relative to the planar support surface, the first print data defining the first profile for forming at least a portion of the first anatomical model that includes the first anatomical features and is configured for the first surgical training task; and constructing, by a manufacturing device based on the first print data, at least a portion of the first anatomical model including the base and the first surgical site, wherein the first profile defines at least one ergonomic feature configuration of the first anatomical model.

2. The method of claim 1, further comprising:

accessing, by the computing device, second image data defining second anatomical features associated with a second surgical training task;

generating, by the computing device, second print data defining a second profile for forming at least a portion of a second anatomical model that includes the second anatomical features and is configured for the second surgical training task; and constructing, by the manufacturing device based on the second print data, at least a portion of the second anatomical model with a second surgical site configured for the second surgical training task, wherein the second profile defines at least one ergonomic feature configuration of the second anatomical model such that, when a bottom side of the second anatomical model rests on a planar support surface, the second surgical site is presented at a predetermined height and approach angle relative to the planar support surface.

3. The method of claim 1, further comprising forming the first anatomical model such that, when the bottom side rests on the planar support surface, the first surgical site is presented at the predetermined approach angle without fixation of the first anatomical model.

4. The method of claim 1, wherein the first anatomical model includes an opening preformed along the first anatomical model along the first surgical site, the opening providing access to the first surgical site to accommodate training of the first surgical training task without a surgeon having to form the opening during training.

* * * * *